(12) United States Patent
Armstrong et al.

(10) Patent No.: US 11,932,863 B2
(45) Date of Patent: Mar. 19, 2024

(54) PLANT REGULATORY ELEMENTS AND USES THEREOF

(71) Applicant: Monsanto Technology LLC, St. Louis, MO (US)

(72) Inventors: Charles L Armstrong, St. Charles, MO (US); Andrei Y. Kouranov, Chesterfield, MO (US); Brent A. O'Brien, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 145 days.

(21) Appl. No.: 17/146,455

(22) Filed: Jan. 11, 2021

(65) Prior Publication Data

US 2021/0238616 A1   Aug. 5, 2021

Related U.S. Application Data

(60) Provisional application No. 62/969,993, filed on Feb. 4, 2020.

(51) Int. Cl.
*C12N 15/82* (2006.01)

(52) U.S. Cl.
CPC ................. *C12N 15/8218* (2013.01)

(58) Field of Classification Search
CPC .................................................. C12N 15/8218
USPC ....................................................... 800/279
See application file for complete search history.

(56) References Cited

U.S. PATENT DOCUMENTS

| | | |
|---|---|---|
| 2006/0141495 A1 | 6/2006 | Wu |
| 2012/0174258 A1 | 7/2012 | Narva et al. |

OTHER PUBLICATIONS

Oommenn et al The Plant Cell 6:1789-1803 (Year: 1994).*
Kim et al. Plant Molecular Biology 24: 105-117 (Year: 1994).*
International Search Report and Written Opinion regarding International App. No. PCT/US2021/013244, dated May 7, 2021.
Rhodora R. Aldemita and Thomas K. Hodges. 2007. Gene expression in transgenic rice with corn pollen-specific promoter Zmg13. Philippine Journal of Crop Science 32(3):3-16.
Laurine M. Gilles, Abdelsabour Khaled, Jean-Baptiste Laffaire, Sandrine Chaignon, Ghislaine Gendrot, Jérôme Laplaige, Hélène Bergès, Genséric Beydon, Vincent Bayle, Pierre Barret, Jordi Comadran, Jean-Pierre Martinant, Peter M. Rogowsky, and Thomas Widiez. 2017. Loss of pollen-specific phospholipase Not Like Dad triggers gynogenesis in maize. The EMBO Journal 36(6):707-717.
Douglas A. Hamilton, Mihir Roy, Julia Rueda, Ram K. Sindhu, John Sanford and Joseph P. Mascarenhas. 1992. Dissection of a pollen-specific promoter from maize by transient transformation assays. Plant Molecular Biology 18: 211-218.
Timothy Kelliher, Dakota Starr, Lee Richbourge, Satya Chintamanani, Brent Delzer, Michael L. Nuccio, Julie Green, Zhongying Chen, Jamie McCuiston, Wenling Wang, Tara Liebler, Paul Bullock, and Barry Martin. 2017. Matrilineal, a sperm-specific phospholipase, triggers maize haploid induction. Nature 542:105-109.
Jinxia Ma, Qian Zhao, Jingjuan Yu* & Guangming Ao. 2005. Ectopic expression of a maize pollen specific gene, zm401, results in aberrant anther development in tobacco. Euphytica 144: 133-140. DOI: 10.1007/s10681-005-5272-2 C.
He Wang, Mingxia Fan, Guohong Wang, Chunyu Zhang, Lei Shi, Zhengyi Wei, Wenjuan Ma, Jing Chang, Senxin Huang, and Feng Lin. 2017. Isolation and characterization of a novel pollen-specific promoter in maize (*Zea mays* L.). Genome 60: 485-495. dx.doi.org/10.1139/gen-2016-0089.
Mayada Woriedh, Sebastian Wolf, Mihaela L. Marton, Axel Hinze, Manfred Gahrtz, Dirk Becker, Thomas Dresselhaus. 2013. External application of gametophyte-specific ZmPMEI1 induces pollen tube burst in maize. Plant Reprod 26:255-266. DOI: 10.1007/s00497-013-0221-z.
Juan J. Estruch, Sue Kadwell, Ellis Merlin, and Lyle Crossland. 1994. Cloning and characterization of a maize pollen-specific calcium-dependent calmodulin-independent protein kinase. Proc. Natl. Acad. Sci. USA 91:8837-8841.
Imelda Lopez, Richard G. Anthony, Sutherland K. Maciver, Chang-Jie Jiang, Safina Khan, Alan G. Weeds, and Patrick J. Hussey. 1996. Pollen specific expression of maize genes encoding actin depolymerizing factor-like proteins. Proc. Natl. Acad. Sci. USA 93: 7415-7420.
Felix D. Guerrero, Lyle Crossland, Gregory S. Smutzer, Douglas A. Hamilton, and Joseph P. Mascarenhas. 1990. Promoter sequences from a maize pollen-specific gene direct tissue-specific transcription in tobacco. Mol Gen Genet 224: 161-168.
Amien, S., Kliwer, I., Márton, M. L., Debener, T., Geiger, D., Becker, D., & Dresselhaus, T. (2010). Defensin-like ZmES4 mediates pollen tube burst in maize via opening of the potassium channel KZM1. Plos Biol, 8(6), e1000388.
Dresselhaus, T., Lausser, A., & Márton, M. L. (2011). Using maize as a model to study pollen tube growth and guidance, cross-incompatibility and sperm delivery in grasses. Annals of Botany, 108(4), 727-737.
Engel, M. L., Chaboud, A., Dumas, C., & McCormick, S. (2003). Sperm cells of *Zea mays* have a complex complement of mRNAs. The Plant Journal, 34(5), 697-707.
Koziel, M. G., Beland, G. L., Bowman, C., Carozzi, N. B., Crenshaw, R., Crossland, L., . . . & Evola, S. V. (1993). Field performance of elite transgenic maize plants expressing an insecticidal protein derived from Bacillus thuringiensis. Bio/ technology, 11(2), 194-200.

(Continued)

*Primary Examiner* — Li Zheng
(74) *Attorney, Agent, or Firm* — Dentons US LLP; Timothy K. Ball

(57) ABSTRACT

The invention provides recombinant DNA molecules and constructs, as well as their nucleotide sequences, useful for modulating gene expression in plants. The invention also provides transgenic plants, plant cells, plant parts, and seeds comprising the recombinant DNA molecules operably linked to heterologous transcribable DNA molecules, as are methods of their use.

15 Claims, No Drawings

Specification includes a Sequence Listing.

(56) References Cited

OTHER PUBLICATIONS

Mao, Y., Zhang, Z., Feng, Z., Wei, P., Zhang, H., Botella, J. R., & Zhu, J. K. (2016). Development of germ-line—specific CRISPR-Cas9 systems to improve the production of heritable gene modifications in Arabidopsis. Plant biotechnology journal, 14(2), 519-532.

Peng, J., Qi, X., Chen, X., Li, N., & Yu, J. (2017). ZmDof30 negatively regulates the promoter activity of the pollen-specific gene Zm908. Frontiers in plant science, 8, 685.

Slotkin, R. K., Vaughn, M., Borges, F., Tanurdžić, M., Becker, J. D., Feijó, J. A., & Martienssen, R. A. (2009). Epigenetic reprogramming and small RNA silencing of transposable elements in pollen. Cell, 136(3), 461-472.

Von Besser, K., Frank, A. C., Johnson, M. A., & Preuss, D. (2006). Arabidopsis HAP2 (GCS1) is a sperm-specific gene required for pollen tube guidance and fertilization. Development, 133(23), 4761-4769.

\* cited by examiner

SEQUENCE LISTING

<160> NUMBER OF SEQ ID NOS: 21

<210> SEQ ID NO 1
<211> LENGTH: 1973
<212> TYPE: DNA
<213> ORGANISM: Zea mays
<220> FEATURE:
<221> NAME/KEY: misc_feature
<222> LOCATION: (1)..(1973)
<223> OTHER INFORMATION: A DNA sequence of a promoter operably linked to
      a leader, P-Zm.GRMZM2G487322:2 derived from Zea mays.

<400> SEQUENCE: 1

```
atttttttat gtcatcctaa tagatctaac tgaactcaaa agattctata ttatccttat      60
gcattcattt tgccctaatt agcatattta tcccactcta gaataacaac catgagctaa     120
tccaaaattt acttagatct taactagtct aatccagtca tatccaacct aatctagatt     180
ttatctaaac tttgatgatc taatcaagag taagttactt aatgcgggta caaaagataa     240
ggccatactc ctagttcact cgagcctaaa ttggtgactt agatcaactc ggccataccc     300
aacaacttga cctacatcat gtaatctatc tcatcctgat ctatcttaac cacactcccc     360
aaccctgatg atatacacta acatcgaatc aatgaggtca agaccggaga ggaaaagatc     420
aacattaaca aggaaggatg taacagtcaa agcgaatctc gagatgaatc aagacttaga     480
catttcagat gaagttttc ctatctttct tacctcaaca tgtccatctt atatcctaca      540
taataagtag ctggatacct atgctctcct aataacatac tattgactat ataaaaaaat     600
gagactctag acttttagaa acaactatag actaaaaaaa tgaattacaa accaatcttt     660
ctatatccct tttgttacta atctcggaga cgagatttct gttaaggggg taggatttgc     720
aacaccctaa tatcccactg ttggtatttg gggaaaatct ttctatagaa tttaaataga     780
tagaccaata gatacccctc ttaaaaatat tattaagata tcccttttaa taataaattt     840
gaagatactc ttaaacaaga ataccttta ataaagatta tatattagag attatattct      900
taaagtaaat aagtaactaa taaatagata cggtaagttt gatctcttga tgataatttt     960
ggtgaagcat tttatggaga acataacatt gacctccaat tctaaataaa cacataaaat    1020
tgtaaatgag aaagggaatg tttatgaaac catttattcc tcccataaat agatggcaag    1080
gaaaaataat aaataatagt aatgtaaaca gtagaagtta tattcacttg ggaatttgaa    1140
gttcaaaatg ggagtttgaa tttgaagtga gaactttgaa atagaaaagg aattttctt     1200 gcctttgaag taattttaa accaatgaaa taatagatgt ttatgcctct aatttagatt     1260
tgacttgtga aattttaaac tgaatttctt tggagcaaaa tcttatctca aactcaattt    1320
atttaattat ttgagttaca tatcttttat atgcctacaa gcattcatct aaatgagaag    1380
taaaaatgat aaattgtatt ttaaccggag tatacatttg aggggttata cctgagaaat    1440
tattcttaaa ttatattatt ttgtgtgtat gaattgtaca tttaaaagca ttggcataaa    1500
taaatgtgat gataaataaa taactaacat aaaatttat cttgcatgcc ggagttttat     1560
gttcttgagc atttaatatt aaaatttaaa ctcatttgaa tttggaatag aaatctaaaa    1620
aaacaaaaaa taaaaaaagc cactcacccct gagccatgac cgctcagcca cccacgtcca    1680
ctttcccatg catgtataac tcaagctggt agacttccct ggttagccgc gttcttagct    1740
taggttagtt ggaagctgcc gagcgaatca ccgtaaccgc accacgagct aaacgcgcgg    1800
ctaccataac catccgccca atctgcggtc tatagattta atgacggctg gttgcatgcg    1860
cccctaggtt gttagccatc gctaataaat actgggctgc tgtgattcct tcgtcacctc    1920
```

```
gaatagccag aaactatcgc cagcaaaggg agaacgccga ggtgagagag ata         1973
```

```
<210> SEQ ID NO 2
<211> LENGTH: 501
<212> TYPE: DNA
<213> ORGANISM: Zea mays
<220> FEATURE:
<221> NAME/KEY: misc_feature
<222> LOCATION: (1)..(501)
<223> OTHER INFORMATION: A DNA sequence of a 3' UTR,
      T-Zm.GRMZM2G487322:2 derived from Zea mays.

<400> SEQUENCE: 2
aatcacggta tgaatcctcg tagctgtttt gcctcagtcc ataggttgct tagcgtgggt    60
aggactgctg tctggatgtg aggttgcgtg tcggtctgcg ccgaccatgg cgccgccgcg   120
aagcctgctg cgcgccaccg cattggatcg acggggagg aagaatcgta ggagccgtcc    180
gatcggtttt gggcgatctg gattagatgt ggtgtaccca ttcgataggt taaatccgag   240
ccgttgatta gatatcagat caactagatc tgatcgcacc ctaataaatc tagatcatag   300
atctttgatc caacggcttg agttgcgtac cggttcacag ttatgaatat ctaatctgat   360
ccgtaggtag tcgatccaac ggcctagata tcgcgtacc ccttcggccg cctatttgc     420 ataagagccc ccggattttc ctaaaaacaa cccgcggtcc agtactggat tcactgagtc   480
tgcgtaaact ttatgcttta g                                             501
```

```
<210> SEQ ID NO 3
<211> LENGTH: 1998
<212> TYPE: DNA
<213> ORGANISM: Zea mays
<220> FEATURE:
<221> NAME/KEY: misc_feature
<222> LOCATION: (1)..(1998)
<223> OTHER INFORMATION: A DNA sequence of a promoter operably linked to
      a leader, P-Zm.GRMZM2G339781:1 derived from Zea mays.

<400> SEQUENCE: 3
cacaagcaca tcgacgtgtt cacgcacacg actagacgtg gagtcgctct acgtgaagac    60
cggtgaggtg ttgttcgtca actccattct gcagctgtat tgcctcttgg ccttcgacga   120
cgactccgac aaggatggct gccactagta gaacagtggc agtagcaggg ataagtggca   180
gctgagccta gagtcatgcg cagacgcgtt cctaggagca ctaaggatta aaatagcggg   240
atatgcaaaa tagcggcttc attttttag gctacaagac tactgcacga ctatggttat    300
aaaagtatta aaaatatgc atgatttatg caaaaaaac atggaattca atatatttga     360
ctaaggtcaa tatgttttca aggctctagg agactagaga tagtacacaa tacatgattc   420
gtggaattaa agtgtttggc acttcaataa catagttggc cactagctag gtagctacac   480
aacatgataa ttaataggtt tacttagttc taaatactaa agtagtaaag aatttactaa   540
ctcgctaaca tggtagcaac acaataccat gatttagtac ataccaaaaa agcttactag   600
tgcaatctat tgatcaagca tagagtcatc tgaataagaa gaatgaatgc ttaggacta    660 ttgatccatg tcaatatcgt gtgcatcatt ttattatgta taaagcaagt ttaggttatt   720
atgtatcaag caagtttaga tttaccttca ttacaataat tcatatcatt gagcttcatc   780
atccttcttc attacattca ttatttgttg gtgcaccatg aaaagtacaa atagtgtggc   840
tatttagcgt taaagataca agctccatgc tagctagagc tcgtttggca gtgctgcgct   900
ccatgattct ctaactccaa gagctgattc tccaatagag tgattctcta gcaaaagtat   960
atctatttga taaaaaccgt ttgacaaata gtctgtgatg tgattcttga ggggttggag  1020
```

```
agtgggagc agcgagaagc aagtttttt tggctcccac cttctagtac aaaacagaga    1080
gtaaattcat tccgctttca ccgtggagca gttcagtttt ttttgctatt tagctacgcg    1140
ggagtgattc tcgctgtgag cgaagctgtt ggagctctac caaacgggta tagaagtatt    1200
acccacgcat gctatcgtta agtacgctgg atggcagaac aatggagtag tatgtgggta    1260
gagtggaatt tttttacat ctgggataca aagaaactct tttgtagctc ttgacatcca    1320
ccacctgatg atccatataa atagaaaaaa aataaattag taaagggtta agttgtaaaa    1380
tttaatctgt ttttgtggcc tttaaataat gtgatgtatg tgagggattg taaaaaagag    1440
tgtttgcatc cagatataga gaaaaatttt ccggctgagt gggggactgg ggcgcacgta    1500
ctgatcggtt gtacgtgcgg atcgcataaa ctgggaccgg agaccgtgct gtggtcgcgc    1560
cgggccaggg cagcgccatg tgaccccttt tctgagctca tgtgaggccg ggcgagccgc    1620
gagccagtat atcgatcgcc ggctgcatgc atgcaagggt ccgaaagaac ggatcgacgt    1680
cggcacgtcg catacacgtg ccgcgcgtga cgaaataact aaaaaagaaa gaaaagatgc    1740 tattttagt ctcagagcac aagctattat tagggatttc cgtgatcaac caatgggtgc    1800
ctggtttcaa ggtcggccgg tgcaactgta gccaattcaa aacagtggag cctagctggc    1860
tacggatccg acacatcgcg catgcacaca tcaactcttg aaagccaacg ccgagacctg    1920
acctgcaggg gctacgcacg tcgtcgtcgg aagttactgc cgtcgtccga ggaaaaccgc    1980
gcgcggccgc cgacgaac                                                 1998

<210> SEQ ID NO 4
<211> LENGTH: 501
<212> TYPE: DNA
<213> ORGANISM: Zea mays
<220> FEATURE:
<221> NAME/KEY: misc_feature
<222> LOCATION: (1)..(501)
<223> OTHER INFORMATION: A DNA sequence of a 3' UTR,
      T-Zm.GRMZM2G339781:1 derived from Zea mays.

<400> SEQUENCE: 4
acgatgatgc acttatgggg ccatgtccac cggagctttt actgtttgcg tgtcgcgccg     60
gtcggcccag cggcggcggt ctatgctccc gatgtgcatg aaaaattccc gctgttttct    120
ttggtgtttg gtatgtacgt tattatgtac gctgcctctt ctcaaagcat agtatgcata    180 gttctgttt ctggcattcg atggccggtt gccccacctc ccctgaaaca cacacaccccc    240 aacacagaca cgcagatacg tacgcacgct ctcagctgca aagtcatcac tgttaggaca    300
tgtgcaacct aaatattact ccctatgttt ataaatatat gactacgttg attttttta    360 aactttgatc acccatctta ttaaaaaaac tttgatttat tttttgtgat ttatttatca    420
cttaaggtag tttgtgctta acttaaaatt ttatatttt gaataaatat tttgaataga    480
caaattgtca aagttttcga a                                              501

<210> SEQ ID NO 5
<211> LENGTH: 2196
<212> TYPE: DNA
<213> ORGANISM: Zea mays
<220> FEATURE:
<221> NAME/KEY: misc_feature
<222> LOCATION: (1)..(2196)
<223> OTHER INFORMATION: A DNA sequence of an EXP, EXP-Zm.Xet:1
      comprised of a promoter operably linked to leader (P-Zm.Xet:1),
      operably linked to an intron (I-Zm.Xet:1) derived from Zea mays.

<400> SEQUENCE: 5
```

```
tgttttgatt aatgagctca gtgaaagtgt ttttcgactt tcggcccgag gccttcattt    60
attccacggt ttgagctcgt tatggaaaca aactaatacc acgagtggct actattggag   120
gccctcttcg gccgaaggtc ctcaaaacat tgtttttata attatctcta aatctgtttc   180
atgtagataa cttttatcga aggttacctt cggatggaga tgaggcacag taacagcgtt   240
ttgcaaaaac gaagctaaaa ggcttcggct cagcggcacg catgcatgac gaagaagtta   300
gcaggagcaa ggcggagtcc tcaagacttg ttcagtaaga actatgaagg aaaggacaa    360
caatacccct aatctgctcc atagttcata tgtatgggtc taagggtatg attgtagttt   420
ccacaaggtt atacccacg actataaata gaggaacaat gttatgcata tggcacgctt    480
ttttgccgga gaagagtgac tcgctccccc tatgaagttc ttttctcttt ctacctacac   540
gttgttgttc atcaaaccta ggtataattg taatcattca tcatataata aaagatggag   600
aaaagtaatg tcgaattaag attagttatc cattatatct tccataccgg attaattgta   660
tacatgacac ttaattttta caaaattaga tggttatttc attttgatgc atggagtgac   720
atgaaaatga agtagtttcc aatttttta aaatttaagt ggcatgtttc taactgaccc    780
ttagtatttt tcatctttg ttcattcttt taaccttatc catttaatta atctctttga    840
gaagggttaa ttaaagggac aaagtaaaaa aagattaatt catgtgtgtt gtcttgttta   900
tgatattctt ccggagttaa aaacaagcgg caaacctaaa gtattgttga acaccaaaag   960
tggtggacgg ttcgtgctct ggcgatcaga ttaactggcg attatcctta tcttgtgcgt  1020
ggttattcat ctaatcacgt gggatttgtt aactatcatc taagaacgga tccagacttc  1080
tccctgtata tatgaagggg tacggccgat tgagaaccc cgaacacatt ccaatcgaac   1140
caatctattt acattatctt tttttattat tcttgtccta ggagtagatg tagcctagtc  1200
ttagttgtag ctttctgcat atccatctcc acccctattc gactctacgt cgtctagatc  1260
catcttaggt ggcctgccga ccctaggatc tcgcccttcc tgaggggcaa tatccaccct  1320
cctcatccct ttaagtaaag atctcttaac ttgattcctt aatttctagg caaatctaca  1380
tcatctagag acgtcccaga tgatctgttg atccggagcg ccctaagatc tttccctagt  1440
gggcgggatc taggacccca cgagaaggaa gacggccatg cgccatcgcg gaccatctaa  1500
ccctgtacgc ggaccgtccg gaacgacgca gggaaggagc agcccctgcc gccaggtcgc  1560
agactgtctg acccaaagcc gcagacaatc tgcgccaccg cagagggcag acggtgaccc  1620
tagtgattgg cgctgcccac gtcagcggca acaaagtatc atttaatgtc ccatttcggg  1680
gtcactcccg aaagtttagc tgcacgtgca gctcgatcac caacacatgt aacgtgcaca  1740
ttgtctattc cgggacacaa gaaacagagt gcctgcgcaa tactcaagcc gattaagccg  1800
cgtttacgtc ggaacagcat ggaggcaggt cttccatgaa gctaacctaa gccagctagc  1860
taacaagtca gcctcccaaa cattgccaag aacaagacct gttcttaata gacaacgaca  1920
gcaagagcaa ggataccaga agctgattct ttggccttgg tcgattggat tgcagagcca  1980
attagctagg tagcagtgcg gaccgcaggt aagtagtgag ttcctccacg gcacggccgc  2040
atctctgatc ggttttccgg tgggcgcggt caccgcgcgc ggcacgcagt caccatttct  2100
gcacaaatat atatgacatg ttgttgaatg catggacgcg acgcgtgccg cgtgcgcatc  2160
gcatgcactg cttggccggt attgcagttt tcaggt                            2196
```

<210> SEQ ID NO 6
<211> LENGTH: 1998
<212> TYPE: DNA

<213> ORGANISM: Zea mays
<220> FEATURE:
<221> NAME/KEY: misc_feature
<222> LOCATION: (1)..(1998)
<223> OTHER INFORMATION: A DNA sequence of a DNA sequence of a promoter operably linked to a leader, P-Zm.Xet:1 derived from Zea mays.

<400> SEQUENCE: 6

```
tgttttgatt aatgagctca gtgaaagtgt ttttcgactt tcggcccgag gccttcattt      60
attccacggt ttgagctcgt tatggaaaca aactaatacc acgagtggct actattggag     120
gccctcttcg gccgaaggtc ctcaaaacat tgttttata attatctcta aatctgtttc      180
atgtagataa cttttatcga aggttacctt cggatggaga tgaggcacag taacagcgtt     240
ttgcaaaaac gaagctaaaa ggcttcggct cagcggcacg catgcatgac gaagaagtta     300
gcaggagcaa ggcggagtcc tcaagacttg ttcagtaaga actatgaagg gaaaggacaa     360
caatacccct aatctgctcc atagttcata tgtatgggtc taagggtatg attgtagttt     420
ccacaaggtt atacccccacg actataaata gaggaacaat gttatgcata tggcacgctt     480
ttttgccgga gaagagtgac tcgctccccc tatgaagttc ttttctcttt ctacctacac     540
gttgttgttc atcaaaccta ggtataattg taatcattca tcatataata aaagatggag     600
aaaagtaatg tcgaattaag attagttatc cattatatct tccataccgg attaattgta     660
tacatgacac ttaattttta caaaattaga tggttatttc attttgatgc atggagtgac     720
atgaaaatga agtagtttcc aattttttta aaatttaagt ggcatgtttc taactgaccc     780
ttagtatttt tcatcttttg ttcattcttt taaccttatc catttaatta atctctttga     840
gaagggttaa ttaaagggac aaagtaaaaa aagattaatt catgtgtgtt gtcttgttta     900
tgatattctt ccggagttaa aaacaagcgg caaacctaaa gtattgttga acaccaaaag     960
tggtggacgg ttcgtgctct ggcgatcaga ttaactggcg attatcctta tcttgtgcgt    1020
ggttattcat ctaatcacgt gggatttgtt aactatcatc taagaacgga tccagacttc    1080
tccctgtata tatgaagggg tacggccgat tgagaaccc cgaacacatt ccaatcgaac     1140
caatctattt acattatctt tttttattat tcttgtccta ggagtagatg tagcctagtc    1200
ttagttgtag ctttctgcat atccatctcc accctattc gactctacgt cgtctagatc    1260
catcttaggt ggcctgccga ccctaggatc tcgcccttcc tgagggcaa tatccaccct    1320
cctcatccct ttaagtaaag atctcttaac ttgattcctt aatttctagg caaatctaca    1380
tcatctagag acgtcccaga tgatctgttg atccggagcg ccctaagatc tttccctagt    1440
gggcgggatc taggacccca cgagaaggaa gacggccatg cgccatcgcg gaccatctaa    1500
ccctgtacgc ggaccgtccg gaacgacgca gggaaggagc agcccctgcc gccaggtcgc    1560
agactgtctg acccaaagcc gcagacaatc tgcgccaccg cagagggcag acggtgaccc    1620
tagtgattgg cgctgcccac gtcagcggca acaaagtatc atttaatgtc ccatttcggg    1680
gtcactcccg aaagtttagc tgcacgtgca gctcgatcac caacacatgt aacgtgcaca    1740
ttgtctattc cgggacacaa gaaacagagt gcctgcgcaa tactcaagcc gattaagccg    1800
cgtttacgtc ggaacagcat ggaggcaggt cttccatgaa gctaacctaa gccagctagc    1860
taacaagtca gcctcccaaa cattgccaag aacaagacct gttcttaata gacaacgaca    1920
gcaagagcaa ggataccaga agctgattct ttggccttgg tcgattggat tgcagagcca    1980
attagctagg tagcagtg                                                  1998
```

<210> SEQ ID NO 7

```
<211> LENGTH: 191
<212> TYPE: DNA
<213> ORGANISM: Zea mays
<220> FEATURE:
<221> NAME/KEY: misc_feature
<222> LOCATION: (1)..(191)
<223> OTHER INFORMATION: A DNA sequence of an intron, I-Zm.Xet:1 derived
      from Zea mays.

<400> SEQUENCE: 7
caggtaagta gtgagttcct ccacggcacg gccgcatctc tgatcggttt tccggtgggc    60
gcggtcaccg cgcgcggcac gcagtcacca tttctgcaca aatatatatg acatgttgtt   120
gaatgcatgg acgcgacgcg tgccgcgtgc gcatcgcatg cactgcttgg ccggtattgc   180
agttttcagg t                                                        191

<210> SEQ ID NO 8
<211> LENGTH: 498
<212> TYPE: DNA
<213> ORGANISM: Zea mays
<220> FEATURE:
<221> NAME/KEY: misc_feature
<222> LOCATION: (1)..(498)
<223> OTHER INFORMATION: A DNA sequence of a 3' UTR, T-Zm.Xet:1 derived
      from Zea mays.

<400> SEQUENCE: 8
aagccctacc aattaatagt gtgattagac atgggcatag ttcatcgaaa cagagaaatc    60
gatccgaaat caaaaccaaa agaaatgata tacggagtac atgaattatg attcacttgt   120
attgtataac tatatttcat ttatgtctga tgtctcacat tgatttgcta tgtatttatt   180
tactgtatta ctattattct cttatcaatt attgttattt aaaatataga ttgtgttgtc   240
taaatttgtt tttaaaacca gcatattgtt ttattctgtt aacatctcct gaaaaggttc   300
ggttaattag attagaacca atggcaaatc tagcacaaaa tatgagtgaa gtcacactta   360
caaaaacaaa cactaaaata tcaaaacgag gacatctaag ttaagctgtg tgacgcacgc   420
ggcacgatgt tgtctggttt catgtgccaa gccataggtg gtggtggccg aagtagcttt   480
gtagctgttg tgtcagtc                                                 498

<210> SEQ ID NO 9
<211> LENGTH: 2183
<212> TYPE: DNA
<213> ORGANISM: Zea mays
<220> FEATURE:
<221> NAME/KEY: misc_feature
<222> LOCATION: (1)..(2183)
<223> OTHER INFORMATION: A DNA sequence of an EXP, EXP-Zm.Sat6:1
      comprised of a promoter operably linked to leader (P-Zm.Sat6:1),
      operably linked to an intron (I-Zm.Sat6:1) derived from Zea mays.

<400> SEQUENCE: 9
ttttttttta attttaaaat acgttttgcc gagtgccaga tcgcgggcac tcgacaaagg    60
cgactttgcc gagtgtcacc tgacaggcac tcggcaaaga gttttctat gttctttgcg   120 agtgtcaacc gactgacact cggaaagcta tctttaccga gtgtcaaaat ttaacactcg   180
gcaaaataca tttaaatttt ttaaattttg tctcccaaac ttttttgtggt atgttcctac   240 actatgtaga cctacatgta tcatttgtgg acaattataa catagtttcc atagttagta   300
gatttagttc gtttatttga atttcttcgg aaaattcaaa tttgaactgc aggtcactcg   360
aaacttggaa aaccgtgcat gaaaaaatga tattcatgtt acttagcata agttacgacc   420
gattgcagaa gcgtaccgga aacttcgagc aacatgctca ctaaacatgg ccgtgaactt   480
```

```
ggcatccaca tgtttaaaaa ttgtataaaa cacacacaaa gtcagaaaat catgaaactt      540
gtccacgtgt catgatatca tatgtatagg ctgtgataaa aattttagaa tgtttggaga      600
aagttgtgag acactatgtg tagacacatg attgtctttg ccgagtgcct acctgtgccg      660
agtgtttagc actcggcaaa gggtctcttt gccgagagcc taactttacc gagtgcgaca      720
ctcggtaaag tcttctttgc cgagtgcccg acaaaggca ctcggcaaag aatacaacac       780
tcggcgaagc tcggattcc ggtagtgtcg tggcattgct tgccaaacca ataggcactt       840
gagctttgca gtcgcacaca ttgttggtct tccggatgtc tagtacagct catggaggtt      900
attgatttct ctagtacaat ctaaactttt atctaaaagc aatatttcat cctctctgtc      960
ttatcacaca atctttggca gtatatcaac taccacacat tctattattt attttcaact     1020
ctcctatcca catccaacta cctaccgacg cacccgcct ctggccccg cctttggccc       1080 cgcccccgag gctcgctgct accctatcca gttgcacaga atggcgcgct gtatgtaggg     1140
ttattcctaa tttcctagcc aaccgtaggt taggtcatct cgagcggtcc gtgtacgtgt     1200
agtgtgtata tggacacgta aaatattgtt tcacactata tactaaattg tttataaagt     1260
ggactttgaa atagatagca ggatagggag gcggctgaag gtatccttat agtgttatct     1320
tttcagtcga ccggtgcaac gtgattccaa ccatatttcc tcaccctccc gtgctcgagt     1380
acggacagcc ttaagctcac atacttgagc aacaatatct tggtgcagat ttccttaagg     1440
taatgcaggg tcttctcgaa acaatgacag ccttctaaat caattacaat taacaattac     1500
ttttatatac agacaaggat aataaatagt acttcctcca ttctttttta tttatcgtgt     1560
tttaattcaa aaaataata gccggtgaca atattcgtaa acggaggtaa tactttataa      1620
cgtaaagata aataataaat aaaaagataa caatttaatt atactaggtg attatataag     1680
aatattgtct ttacttatgc atctaaaata ttggagaagt gcattataca tgtgttattt     1740
tgtagctgtg tgatgcgcgt gctatgttta ggcgtggtga ttcccctcct ccgatccgat     1800
ccattctttg cacccaata acaaccagga tgcgctgtag gctgtagctt ctccttccta     1860
tggatagcat aatgatgtcc gaaacgggaa aacgacgaga gcttccacct ccctcctccc    1920
cgtcccggcc gctctctgca gggcaggcc atgcgggtga ggtaccggtg acgacgcggc     1980
ggcccacggc cggagacgcg gaccgcaggt aagtagtacg tacgttaatt aaatgatgat    2040
atgggtatga ttagaagcta gctaccgcga tcgttgctag ctagtagtaa ctagcaattg    2100
cgatcgagga ttccctcgtg gccgatcctg atgtgtggtt gtctgagacg cgcgtggtgc    2160
tggtgtggcg gcagtttgca ggt                                            2183
```

<210> SEQ ID NO 10
<211> LENGTH: 1998
<212> TYPE: DNA
<213> ORGANISM: Zea mays
<220> FEATURE:
<221> NAME/KEY: misc_feature
<222> LOCATION: (1)..(1998)
<223> OTHER INFORMATION: A DNA sequence of a promoter operably linked to
      a leader, P-Zm.Sat6:1 derived from Zea mays.

<400> SEQUENCE: 10

```
ttttttttta attttaaaat acgttttgcc gagtgccaga tcgcgggcac tcgacaaagg       60
cgactttgcc gagtgtcacc tgacaggcac tcggcaaaga gttttctat gttctttgcg      120 agtgtcaacc gactgacact cggaaagcta tctttaccga gtgtcaaaat ttaacactcg      180
gcaaaataca tttaaatttt ttaaattttg tctcccaaac ttttttgtggt atgttcctac    240
```

```
actatgtaga cctacatgta tcatttgtgg acaattataa catagtttcc atagttagta    300
gatttagttc gtttatttga atttcttcgg aaaattcaaa tttgaactgc aggtcactcg    360
aaacttggaa aaccgtgcat gaaaaaatga tattcatgtt acttagcata agttacgacc    420
gattgcagaa gcgtaccgga aacttcgagc aacatgctca ctaaacatgg ccgtgaactt    480
ggcatccaca tgtttaaaaa ttgtataaaa cacacacaaa gtcagaaaat catgaaactt    540
gtccacgtgt catgatatca tatgtatagg ctgtgataaa aattttagaa tgtttggaga    600
aagttgtgag acactatgtg tagacacatg attgtctttg ccgagtgcct acctgtgccg    660
agtgtttagc actcggcaaa gggtctcttt gccgagagcc taactttacc gagtgcgaca    720
ctcggtaaag tcttctttgc cgagtgcccg acaaaaggca ctcggcaaag aatacaacac    780
tcggcgaagc ctcggattcc ggtagtgtcg tggcattgct tgccaaacca ataggcactt    840
gagctttgca gtcgcacaca ttgttggtct tccggatgtc tagtacagct catggaggtt    900
attgatttct ctagtacaat ctaaactttt atctaaaagc aatatttcat cctctctgtc    960
ttatcacaca atctttggca gtatatcaac taccacacat tctattattt attttcaact   1020
ctcctatcca catccaacta cctaccgacg gcacccgcct ctggccccg ctttggccc    1080 cgcccccgag gctcgctgct accctatcca gttgcacaga atggcgcgct gtatgtaggg   1140
ttattcctaa tttcctagcc aaccgtaggt taggtcatct cgagcggtcc gtgtacgtgt   1200
agtgtgtata tggacacgta aaatattgtt tcacactata tactaaattg tttataaagt   1260
ggactttgaa atagatagca ggataggag gcggctgaag gtatccttat agtgttatct   1320
tttcagtcga ccggtgcaac gtgattccaa ccatatttcc tcaccctccc gtgctcgagt   1380
acggacagcc ttaagctcac atacttgagc aacaatatct tggtgcagat ttccttaagg   1440
taatgcaggg tcttctcgaa acaatgacag ccttctaaat caattacaat taacaattac   1500
ttttatatac agacaaggat aataaatagt acttcctcca ttcttttta tttatcgtgt   1560 tttaattcaa aaaataata gccggtgaca atattcgtaa acggaggtaa tactttataa   1620
cgtaaagata aataataaat aaaaagataa caatttaatt atactaggtg attatataag   1680
aatattgtct ttacttatgc atctaaaata ttggagaagt gcattataca tgtgttattt   1740
tgtagctgtg tgatgcgcgt gctatgttta ggcgtggtga ttcccctcct ccgatccgat   1800
ccattctttg caccccaata acaaccagga tgcgctgtag gctgtagctt ctccttccta   1860
tggatagcat aatgatgtcc gaaacgggaa aacgacgaga gcttccacct ccctcctccc   1920
cgtcccggcc gctctctgca gggcaggccc atgcgggtga ggtaccggtg acgacgcggc   1980
ggcccacggc cggagacg                                                 1998
```

<210> SEQ ID NO 11
<211> LENGTH: 178
<212> TYPE: DNA
<213> ORGANISM: Zea mays
<220> FEATURE:
<221> NAME/KEY: misc_feature
<222> LOCATION: (1)..(178)
<223> OTHER INFORMATION: A DNA sequence of an intron, I-Zm.Sat6:1
      derived from Zea mays.

<400> SEQUENCE: 11

```
caggtaagta gtacgtacgt taattaaatg atgatatggg tatgattaga agctagctac     60
cgcgatcgtt gctagctagt agtaactagc aattgcgatc gaggattccc tcgtggccga    120
tcctgatgtg tggttgtctg agacgcgcgt ggtgctggtg tggcggcagt ttgcaggt      178
```

<210> SEQ ID NO 12
<211> LENGTH: 498
<212> TYPE: DNA
<213> ORGANISM: Zea mays
<220> FEATURE:
<221> NAME/KEY: misc_feature
<222> LOCATION: (1)..(498)
<223> OTHER INFORMATION: A DNA sequence of a 3' UTR, T-Zm.Sat6:1 derived
       from Zea mays.

<400> SEQUENCE: 12

```
tgatcgagcg catgcacgca ggggaacgag gggacgggtc gagaagaagc agatgctgcc    60
gtgttctcag tctctcagct cgatcgagaa tgtgatttgt gcgtgtgcaa ttttgcgtga   120
tgtgtcgtac gtaagtgtaa gtcgtagcat cagcttcgtt ctcctcgtat atgtctggaa   180
atgggatgcc attctacttc cggtgcatgg taccctgtag ttcaaggatt catgtatata   240
tatagcagta ttatacacat atgcatatac atagcaggct gcctatgcac atgaattggt   300
gtctagtccc atgttggtat acatatataa atgggttcta tagttagatt ttgtgggatt   360
attagtccaa tagagaaaat caattaaatc ctagaaaatc tcaaagcctc gtgtatgaca   420
aggggatggt ggaaacaata atcccacatt actaatttaa gtggacctag ctagactagt   480
ttataggtca cctgatcg                                                 498
```

<210> SEQ ID NO 13
<211> LENGTH: 2145
<212> TYPE: DNA
<213> ORGANISM: Zea mays
<220> FEATURE:
<221> NAME/KEY: misc_feature
<222> LOCATION: (1)..(2145)
<223> OTHER INFORMATION: A DNA sequence of an EXP,
       EXP-Zm.GRMZM2G049726:1 comprised of a promoter operably linked to
       leader (P-Zm.GRMZM2G049726:1), operably linked to an intron
       (I-Zm.GRMZM2G049726:1) derived from Zea mays.

<400> SEQUENCE: 13

```
cttcactcgt cggctcgagg accccccggt ctcgaaacac cgacacgtag acgtttggaa    60
acttggcccc actcgtagcc tctaaggatg tagtgggcct aagggccact attagcgccc   120
atgggtacat gtaccctaag cgctacaaac aaaggcccac atagagaaga caggctatga   180
gctccactta tgaggtggtt taaagtgaca agatgcctat gaagaaatag aggtataatt   240
gactgaggcc ctgaccacat agtagctagg gcgccctcca ccacttagga cataagtggg   300
cacccttcca caacgacact taccagccaa atgaagagct ctgaatgcga cacatagcct   360
agcctggcct ggtcccactt ggacctccat agggtaccag ccgagtgcca catgtacata   420
aataagaaat ggaaggctcc ggaccctct aatgggatcc ggacctgctc ccataaatat    480
tgggcaagac taggagcccc taggcacctg aacgctagag gccaccgatg caaaatgggg   540
tctaggcaca ccaaatgtcc cctagatcat cgtgaaaact gtggtcaatg gaggaccact   600
cgtccataga ctggagggct ctgataatgc cacctggctc cgtcaggccc tacgccccca   660
atggggtcca ggaaagccac acgcccttct gaccatgctg cgtacccgat caaggggatg   720
gcagagttag aagacatgcg ggttgtacct gactgggcgg gcacaactat agacgcccat   780
aaccgtctcc tcgttaccag gatccattac tacatgctcc aaaaatatct cagtggcatt   840
ttggtcggtg ctcacacacc tagctacgta gtcaaagaca atattaatga tcgcgtacca   900
gtcatgccac ttctccaaac ctccatggcg tgtgtgaccc caaatatcta cagtgtgctc   960
```

```
cactttgttc aaggacacct atagtagtat ggaaggcgta cttcttcgac tatcacctct    1020
ctagatctct tgtacagcc tccggggtgc tagatatgat catctaaaaa ccagaatgta    1080
caactacaac aattcatatg acatcgacaa atagtaaagt aggggagtta tggcttgact    1140
cacacctaac taatgtacct atcctttccc ttggtctata aaaggaaaag cacggtctca    1200
gtaaaagggg caagcaggac agaattagac tggctaaggc aagtaacaca agcccaagca    1260
atacaattta agaggacgt aagctattat aattaccttc cgccggcatg aacctctcta    1320
aaaactttct tgttctcgta tgaaatcccc aatagagtcc ggttagtggt agcaccgatc    1380
cttagtccaa aaccaggcc atctgagcgc tagcaaacca aatctcata gctaaacttt    1440 acctagacga cgtcgatttt tctacaaaac gacaaccaag aatgagagga gtttttttaa    1500
aaaaaaacac acacacacaa tcgggcacga ttagatctga ttttgaaagt ttgaatttta    1560
tatgtgtata tatgcaagtg taccagttct ttgtttaccg gccggatatc atgtcatccc    1620
tttttgtgtg tactagtcag gtgttttctc cgtgcttcaa gataacgggt tgtccgcagt    1680
tcgcagcctc taaaacatgt gaataccaac tcgacagcgc catgatctat gtatagcaga    1740
tacgcagcta cagactacag tgattctgat tcaatttgag catgtttatt cttttgtttt    1800 tctgtttta ggcatggcag ccactggcac aatatatagc ctaacgtgtc tcttcgtggc    1860
cgaggctagc tgcagggttg gcgttcggcc ggccgtacgc accgtacggc ggcgcggcgc    1920
cttccttccc taccctacaa cgacgatcga cgatgtgcta gccaccccga ccgacacatc    1980
catccagcgg tgcccacccg accgcaggt aagtagtacg tatatatgtt gccctagact    2040
atatatatat acgtatccag catatctcct gctggcgcat gcatgcggca tatatatgta    2100
acaagcaagc atgtgtggcg gcggcattga tggcagtttg caggt                   2145
```

<210> SEQ ID NO 14
<211> LENGTH: 1998
<212> TYPE: DNA
<213> ORGANISM: Zea mays
<220> FEATURE:
<221> NAME/KEY: misc_feature
<222> LOCATION: (1)..(1998)
<223> OTHER INFORMATION: A DNA sequence of a promoter operably linked to a leader, P-Zm.GRMZM2G049726:1 derived from Zea mays.

<400> SEQUENCE: 14

```
cttcactcgt cggctcgagg accccccggt ctcgaaacac cgacacgtag acgtttggaa     60
acttggcccc actcgtagcc tctaaggatg tagtgggcct aagggccact attagcgccc    120
atgggtacat gtaccctaag cgctacaaac aaaggcccac atagagaaga caggctatga    180
gctccactta tgaggtggtt taaagtgaca agatgcctat gaagaaatag aggtataatt    240
gactgaggcc ctgaccacat agtagctagg gcgccctcca ccacttagga cataagtggg    300
cacccttcca caacgacact taccagccaa atgaagagct ctgaatgcga cacatagcct    360
agcctggcct ggtccacttt ggacctccat agggtaccag ccgagtgcca catgtacata    420
aataagaaat ggaaggctcc ggaccctct aatgggatcc ggacctgctc ccataaatat    480
tgggcaagac taggagcccc taggcacctg aacgctagag gccaccgatg caaaatgggg    540
tctaggcaca ccaaatgtcc cctagatcat cgtgaaaact gtggtcaatg gaggaccact    600
cgtccataga ctggagggct ctgataatgc cacctggctc cgtcaggccc tacgccccca    660
atggggtcca ggaaagccac acgcccttct gaccatgctg cgtacccgat caaggggatg    720
gcagagttag aagacatgcg ggttgtacct gactgggcgg gcacaactat agacgcccat    780
```

```
aaccgtctcc tcgttaccag gatccattac tacatgctcc aaaaatatct cagtggcatt      840
ttggtcggtg ctcacacacc tagctacgta gtcaaagaca atattaatga tcgcgtacca      900
gtcatgccac ttctccaaac ctccatggcg tgtgtgaccc caaatatcta cagtgtgctc      960
cactttgttc aaggacacct atagtagtat ggaaggcgta cttcttcgac tatcacctct     1020
ctagatctct ttgtacagcc tccggggtgc tagatatgat catctaaaaa ccagaatgta     1080
caactacaac aattcatatg acatcgacaa atagtaaagt aggggagtta tggcttgact     1140
cacacctaac taatgtacct atcctttccc ttggtctata aaaggaaaag cacggtctca     1200
gtaaaaaggg caagcaggac agaattagac tggctaaggc aagtaacaca agcccaagca     1260 atacaatttta aagaggacgt aagctattat aattaccttc cgccggcatg aacctctcta     1320
aaaactttct tgttctcgta tgaaatcccc aatagagtcc ggttagtggt agcaccgatc     1380
cttagtccaa aaaccaggcc atctgagcgc tagcaaacca aaatctcata gctaaacttt     1440
acctagacga cgtcgatttt tctacaaaac gacaaccaag aatgagagga gttttttaa      1500 aaaaaaacac acacacacaa tcgggcacga ttagatctga ttttgaaagt ttgaatttta     1560
tatgtgtata tatgcaagtg taccagttct ttgtttaccg gccggatatc atgtcatccc     1620
tttttgtgtg tactagtcag gtgttttctc cgtgcttcaa gataacgggt tgtccgcagt     1680
tcgcagcctc taaaacatgt gaataccaac tcgacagcgc catgatctat gtatagcaga     1740
tacgcagcta cagactacag tgattctgat tcaatttgag catgtttatt cttttgtttt     1800
tctgttttta ggcatggcag ccactggcac aatatatagc ctaacgtgtc tcttcgtggc     1860
cgaggctagc tgcagggttg gcgttcggcc ggccgtacgc accgtacggc ggcgcggcgc     1920
cttccttccc taccctacaa cgacgatcga cgatgtgcta gccaccccga ccgacacatc     1980
catccagcgg tgcccacc                                                  1998

<210> SEQ ID NO 15
<211> LENGTH: 140
<212> TYPE: DNA
<213> ORGANISM: Zea mays
<220> FEATURE:
<221> NAME/KEY: misc_feature
<222> LOCATION: (1)..(140)
<223> OTHER INFORMATION: A DNA sequence of an intron,
      I-Zm.GRMZM2G049726:1 derived from Zea mays.

<400> SEQUENCE: 15
caggtaagta gtacgtatat atgttgccct agactatata tatatacgta tccagcatat       60
ctcctgctgg cgcatgcatg cggcatatat atgtaacaag caagcatgtg tggcggcggc      120
attgatggca gtttgcaggt                                                 140

<210> SEQ ID NO 16
<211> LENGTH: 501
<212> TYPE: DNA
<213> ORGANISM: Zea mays
<220> FEATURE:
<221> NAME/KEY: misc_feature
<222> LOCATION: (1)..(501)
<223> OTHER INFORMATION: A DNA sequence of a 3' UTR,
      T-Zm.GRMZM2G049726:1 derived from Zea mays.

<400> SEQUENCE: 16
ccgattacgc agttctatcg ccggcccata ggatcggatt ggatctatca ttcgcgaccc       60
aaagggcctg ttcgtttctg ttgggtttca caaaaattat tccggctaat taaaccttat      120
ataaattaga caagcaatct acataggaat tgttccgagt gttcaattct ctggaaccga      180
```

```
acaaggccta atactttttt tgaaagcacg ttcttattat acacatgtaa caggaaagca      240
cgtagacggt ggtgtaggtt tggtgaggtg agaaacggga ggtcttgcct tcctattgat      300
ttttcatcga tctgtgttgt ttttatttac gccattggcc gacattattt aatgatgtca      360
tgagccatgt ggtatacatg agcatgcatc tccaccgcac ctaacatgtt catgttaggg      420
ctagttcgtt ttcagctgaa tccatgtgga ttggatggaa ttatgtgggt ttaaatccat      480
agcaagtcaa aatctctact a                                               501

<210> SEQ ID NO 17
<211> LENGTH: 1998
<212> TYPE: DNA
<213> ORGANISM: Zea mays
<220> FEATURE:
<221> NAME/KEY: misc_feature
<222> LOCATION: (1)..(1998)
<223> OTHER INFORMATION: A DNA sequence of a promoter operably linked to
      a leader, P-Zm.GRMZM2G141762:1 derived from Zea mays.

<400> SEQUENCE: 17
tgcccgggtc ggggccggaa gtcgcgcgtg gggcctgtcc atcgaacaaa agcgagagaa       60
aacgtgcatc ggccggtggt ggcccgtacg gtgggctggg ctcgaatcaa cagcagatga      120
attggtagac aagacagcgc gatgcatgaa tagtgcgtga ttgggcttct cgagatagac      180
gcggttaatt gggccggatt gcacacgcaa aaacaaaaaa aaaaaactgt cggcgtttgc      240
agttgcagtt gggcagtgtg cacacacgtt aacaacagca gaagcagcaa atgacacggc      300
tcggctcatc aattagctgc tgccacaaac aagggtttac ctgtcggctc atcaattagc      360
tactactaat aatcagcagc gctcggcact ctggcagcac aagcgcagga cccaccagta      420
ctgtgtgcgt gacagcgtga gtactgagtt gggaagccac accccacacc acacggcgta      480
ttggctgtca accgacccgg atcgatcgac tagttgcggt tgccgtcggt tgctcggaca      540
ctcagccctg tcaaggtagc agtactcctc ccggccttat cactccggtg cagtgcagtg      600
gaaacaaaag gcagaaatcc ctaccacggc ggcgcattga tgaatccccg ctgctgtgac      660
tcagagcctg acgaggggggt gctatgctac ggcctactcc gggctagggt gtggagcgag      720
tgtctgggac tgggagaatc cagcgtcgtg tactgtccac gcgtacgcgg ttctcggca       780 aggccaagtg ggcaacatgg cagggtggca agacggtact gtatgtacct accggcacta      840
cgcttcgacg cctccttttt tccaaaacct tccaagcccc gcgttcaaac tgtgcctagg      900
cgacggatcc tcggtgctag tagatacacac acacacacac acacacgggc gaaatgtcgg    960
cgagttaatg acggtggtta aagtgaaacc tggatccagc accagcagca gtctttcagg     1020
tttcaagaac actcaggtcc tgcgttactg tggactgtgg taaaagtgcc ggaagttcag     1080
ttcgacgggg gaagaaaaga agggccgcac ctgcacacag cacacctact acactagtac     1140
actgctgcaa tgtactacct gggccgtgct ccaaaagtcg taaccactcg gagacttccc     1200
tctgtcctat ctccgatcac tgatacatct cacaccctca ccacaccgtg acataatttg     1260
ccagtagggt ttacggtgcg gtatcgataa taaccacact acttgcacaa cagctcactt     1320
cttcgttatt ttttttttgt caagtggggt cgatctggcg ctgcctatga ttcaagtgtg     1380
agaattcagc aacagccagc cagctcctgt ttccgtgtac atacgctttc taaaagctgg     1440
accaggccgg cccaatgctc cagttgcccg tgcgcgctgc ttcgcccct accccaggcc      1500 tagccgcacg gaaatgaatg cgggcccact gcccggacga cttgcaacta gtctccaccc     1560
tgttcaatta aatccacaga cgctgggaaa acaattcttt ttgaaaggta gaaataaata    1620
```

-continued

```
aaagattgtg ggctgttgaa gtgcaatcta acccctttct cagactatct tctaaataac    1680
tacttttcgc agaatcaggc gtgtcatctc tagacgatga gattacacca gtcagctaca    1740
gatgacgaat ctgattaaaa aaaatttggt gctagtatac tctaatcgtt ttacgctaga    1800
tatgttgtca ttaattaatt gataaaaaaa aaacaatatt tgtaactgat gccatgcatg    1860
cagcaggctg cacggcacgg tcgtccggaa ctccggatga tgatataaga ccagcgtcac    1920
ccccgcgcgc gcagcctgct gtgatgcgcc caagtcgatc aatcatcgtc cgctctcatc    1980
atctcatcgc aaagccaa                                                  1998
```

<210> SEQ ID NO 18
<211> LENGTH: 1568
<212> TYPE: DNA
<213> ORGANISM: Zea mays
<220> FEATURE:
<221> NAME/KEY: misc_feature
<222> LOCATION: (1)..(1568)
<223> OTHER INFORMATION: A DNA sequence of a promoter operably linked to a leader, P-Zm.DSUL:1 derived from Zea mays.

<400> SEQUENCE: 18

```
tttgctcaca ggtgactcag tagatgacga tcatgatgcg ctttaggtca tatatttgaa     60
gttcatcact gacctcatca aggaacatgt ttctagtgac cttggtgtta gggtgttctt    120
atggggtcgt aggtcatgct accatcactg tcgatcgagg cattgtagga atcgttcagt    180
caagtcattg accgcccttc actcaatcag tcattgaccg cccatcactc aaccaggtca    240
cgagtacctg acttatgcat gggacaatac ttcctttact aggtgcgata aggcactata    300
tggcaatggt tgtcttcatg ggggtaggct cgatgtcact ctgaagtcac aaccctaggc    360
gtgataccat acttttttg tgcaatagat agagcaactc gtaggtcatg gatcttagag     420
ttccaagggc ccttaagggg ggtctaggcg atcaagagga ctcaaggaga atgagagcgt    480
cttggagtgt cctaggggcc ttgagtgccc tctgtttcac ttgttctaac aaatggttgt    540
ggctgggata gtcttacatg tctacggagg cccgagacca gatcctctga tatgttaggc    600
ttgtatctta gctagagtcg aggttagtcg cggatcagac aattccttct atcgaggttc    660
tttgaaaggc atcctatcaa ctcattaggg tatgatctac tcccgttgtt aataaacgta    720
ttttataaca caacactcac atcatgaatt gtatttaaac tcaaccagaa cttcagcatc    780
tcctcaccag tatgaatcat cacatattca tcaacgatgt tttcagagtc catgcctcta    840
aataaattta ttataaaaaa tattctataa ctaatctaat aatacttatt ttatattaaa    900
aaattagtac ttatataact ttagtcaaag ttcaaactgt ttgaggaagc caacattata    960
ctttttatgg atggttgaag tatacagttt tctataaact ttgtcaaatt atgtatggta   1020
acttaactta gaaaataaca agaaataatg gagagatatc acatttggaa acggcgtagt   1080
attccacttg gaacactttt attttaagat gcaaaaaaaa atggctggtg gagctaaaat   1140
attttttatt tgagccgaga cattcttttt ttgtgaacta cttcatctgc gcagcggcag   1200
acttcgcgtg cgtattaatg tttatactgt gttgaacttt agatacataa accgataaac   1260
gcatgcaaat taaagttgt tcttgctgcc acgcctatcg gttgagttgc atgactttca    1320
ggccaacaca ctgcaagcaa aatggaattg agatttact acgagagcga gtggtcaagt    1380
attcatgact agccggctgc ctcgtcttct tctcgaatgg aatggctccc acttgctgca   1440
aacgccccgc cggagacgct tcgttacccc actaatccct ggaaaggagt ttacatggac   1500
agtgggagcc tatataagca cgttcatggc gagacactac atccgagaag gacgatcagg   1560
``` cttcaggc 1568

<210> SEQ ID NO 19
<211> LENGTH: 2000
<212> TYPE: DNA
<213> ORGANISM: Zea mays
<220> FEATURE:
<221> NAME/KEY: misc_feature
<222> LOCATION: (1)..(2000)
<223> OTHER INFORMATION: A DNA sequence of a promoter operably linked to
a leader, P-Zm.GRMZM2G512113:1 derived from Zea mays.

<400> SEQUENCE: 19

| | | | | | |
|---|---|---|---|---|---|
| ccttccttcc | atatttactt | cttatttcaa | ccaaaccaag | atgttaggtt | ttaggcccag | 60 |
| aaccatgcat | atgactgatt | gtaagctgta | ggcacagatg | ccaatgtgtt | ttttttttct | 120 |
| gttttcaact | tttaatgact | acatctctgc | tgagggtggc | gggtgatgag | caacctgtct | 180 |
| ctttatttat | aacaaactca | taccaagaat | gacaggtgct | tttgcttcta | tatttgttga | 240 |
| tctactatat | ttgcttctat | attgggagtt | caatataatg | attaagtaat | ataagtctcg | 300 |
| ggatatattt | tagttgatct | actatatttg | ttgtctgatt | ggaatcctaa | tacttttgtt | 360 |
| aaattatttt | tgttgaccta | atactttcaa | gtaactgcag | attacttctg | tgaaaattat | 420 |
| acggaacaag | cagactgggc | actcagaagg | ctatggtttt | attgagtttt | cctctcgagc | 480 |
| tactgcagaa | catactctga | taaacttcaa | tcggcagatg | atgtcgaatg | ttgagatgac | 540 |
| ttttaagctg | aactgggctt | ctgctagcac | tggtgataag | cgtggagata | gtggttctga | 600 |
| tcacacaata | tttgttggtg | atttggctca | tggtgttact | gactccatgt | tggaagatgt | 660 |
| gttcagagct | aagtacccct | cagttagagg | agctaatgtt | gttgttgata | cttgatagga | 720 |
| tgactggatg | gcccaaagga | tatggtttcg | tgcgttttgg | agatctgaat | aatgcattgt | 780 |
| gaagatgtac | atttgtgctt | gtttgatctg | aaaaggggac | aacttttaga | tatagcataa | 840 |
| taggatatga | agatgaaaga | tctgtactta | gaaatttgtt | catgaatgct | ttgtttgaca | 900 |
| tttaacttcg | tatgctggca | tctcagtgta | ttaagtgtta | atgttacaat | tattcttgga | 960 |
| tcaacaccat | tcgagtattt | gactattgtt | tgtcacgtgc | acttattatt | cttgcatcgc | 1020 |
| tattttgaac | caatttttaa | gttaccgtag | caacgcaaaa | cttgatctga | gtgactgatc | 1080 |
| gtgagctaat | gtaacagtat | gaattatatg | gcttgaacat | ggtaggtgta | aaatgttttg | 1140 |
| ttcatcggta | gagtattcca | gatgtgatcg | gcttaacagt | atgaaatata | tagaactatg | 1200 |
| tgagccaatg | taacagtatg | aattatataa | gttatcaaga | tattatatgc | cctcgttgca | 1260 |
| acgcacgggc | actgacttat | tatgataata | tttgttgttc | tgtatctatg | tttcgtacta | 1320 |
| attttttact | cccgtggcaa | cgcacgggca | cgaacctagt | agaaagtgat | aggagcaaaa | 1380 |
| tggaaagcga | ggagtgtaaa | tgaactcaga | ttctaggatt | ttttaatcga | ttgaattttt | 1440 |
| ttatttcaaa | taattaaaaa | tacatttgtc | tgacgtgatg | ctgtgcatat | ggatcaatca | 1500 |
| gaacatgtga | catcgtaaaa | gcagtcgggc | taaggttcaa | atcggtact | gacacgtcac | 1560 |
| gtcagctgta | tcgagcgaag | gataatatcc | gacatcagtt | ctaacatgat | tggtactacc | 1620 |
| aactagactg | atcgatcgac | ggacctaccg | atcggtgttg | gagtcgaaac | gatcggtacc | 1680 |
| gaccattgac | tcgcctagtc | atagcccatt | gttagaacaa | gacttagaca | aatacacggt | 1740 |
| agatcatctc | tccaattttt | ttcaagaaga | aaaaaaata | gaatttgaga | taactagtcc | 1800 |
| cgacctccca | agggaacatt | tttaacagga | cgcctgcttc | ctcccttttg | ccctcggcag | 1860 |
| ccataactca | tccgggaccg | tcctctccct | ccctccgtct | cgccctatat | aaaggcagac | 1920 |

```
tagctagctc tttcttctcc accgtcgttc ttgccacaca cctgaccgac cttgcctcct    1980
ctccctccta tgccaccaaa                                                2000

<210> SEQ ID NO 20
<211> LENGTH: 704
<212> TYPE: DNA
<213> ORGANISM: Zea mays
<220> FEATURE:
<221> NAME/KEY: misc_feature
<222> LOCATION: (1)..(704)
<223> OTHER INFORMATION: A DNA sequence of a 3' UTR,
      T-Zm.GRMZM2G512113:1 derived from Zea mays.

<400> SEQUENCE: 20
cggcgctatc cttaccgagc tttcatgcat gtaccacgcc ctctttcctc ttcgcagtct      60
ttgtttcatc actcagcaga attcacgatg tatgtcttct tgaccttgca agacttttcg     120
ctagaggatg aatcccaact tcttgtgcct ttccatctcg cacctatcaa tcctcccatc     180
ttcttcgtct ccgtctatcc ctcttgagct tgtaccgctt tgcagttata gctagctagc     240
tagctacgcc tacttccgcg tggactccgc tctctggaag taagtgtctc ctcgtcgcgt     300
gctgccgtgc attgtgttgc cggccggcag ctacttccgc acgaactcta ctagtacgct     360
attattctgt gtaatggaag gtttgtgatg tactccctgt ttatttgcta gttgtccatc     420
gcctttcagc ggaggcagca atagcttgag ctttgctact cgtgtaatta tacgtctcgg     480
aaatgcagtt attagttgtt cccgatgtgt tgtgttgtgt tgtgtctcat tcaggcactc     540
tgtgccatgc agttgcttga tctgtgtgtg tatgcctgtt ctcgctagtc atgtcttctt     600
gtcccaggtg aggcctggcc tgaggaagaa gggggggtagt attcaaccgg ttgaaacaca    660
agtcagccca gcgccactga agtactgaac tgaggctaac ttat                      704

<210> SEQ ID NO 21
<211> LENGTH: 2001
<212> TYPE: DNA
<213> ORGANISM: Artificial
<220> FEATURE:
<223> OTHER INFORMATION: A synthetic coding sequence optimized for plant
      expression for beta-glucuronidase with a processable intron
      derived from the light-inducible, tissue-specific St.LS1 gene.

<400> SEQUENCE: 21
atggtgaggc ccgttgagac cccgactagg gagatcaaga agctggacgg cctctgggcc      60
ttctccctcg accgtgagaa ctgcggcatc gaccagcgct ggtgggagtc cgccctccag     120
gagtctaggg ccatcgccgt gcccggttcc ttcaacgacc agttcgccga cgccgacatc     180
cgcaactacg cgggcaacgt ctggtatcag cgcgaggtgt tcatcccgaa gggctgggcg     240
ggccagcgca tcgtgctccg cttcgacgcc gtgacccact acggcaaggt ctgggtgaac     300
aatcaggagg taagtttctg cttctaccctt tgatatatat ataataatta tcattaatta    360
gtagtaatat aatatttcaa atatttttt caaaataaaa gaatgtagta tatagcaatt      420
gcttttctgt agtttataag tgtgtatatt ttaatttata acttttctaa tatatgacca     480
aaatttgttg atgtgcaggt gatggagcac cagggcggtt acaccccgtt cgaggccgac     540
gtgacgccgt acgtgatcgc cgggaagtcc gtccgcatca ccgtctgcgt gaacaatgag     600
ctgaactggc agaccatccc gcctggcatg gtcatcaccg acgagaacgg caagaagaag     660
cagtcctact tccacgactt cttcaactac gctggcatcc accgctccgt gatgctctac     720
accactccca acacctgggt ggacgacatc accgtggtca cccacgtggc ccaggactgc     780
```

-continued

```
aaccacgcct ccgtggactg gcaagtcgtt gccaacggcg acgtcagcgt cgagctgcgc      840
gacgccgacc agcaagtcgt tgccaccggc cagggcacca gcggcaccct ccaagtcgtc      900
aaccctcacc tctggcagcc tggcgagggc tacctctacg agctgtgcgt caccgccaag      960
agccagactg agtgcgacat ctaccctctc cgcgtcggca tcaggagcgt cgctgtcaag     1020
ggcgagcagt tcctcatcaa ccacaagcct ttctacttca ctggtttcgg ccgccacgag     1080
gacgctgacc tgaggggcaa gggtttcgac aacgtcctga tggtccacga ccacgctctg     1140
atggactgga tcggtgccaa cagctacagg accagtcact acccgtacgc tgaggagatg     1200
ctggactggg ctgacgagca cggtatcgtc gtgatcgacg agactgctgc ggtcggtttc     1260
aacctgtctc tgggcattgg tttcgaggct gggaacaagc cgaaggagct gtactctgag     1320
gaagctgtca acgcgagac tcagcaagct catctccagg cgattaagga gctgattgcc      1380
agggacaaga accatccgtc tgtcgtgatg tggtctattg cgaatgagcc ggacaccaga     1440
ccgcaagggg cgcgtgaata cttcgcgccg ctggcggagg cgactcgcaa actggaccca     1500
acccgtccaa tcacgtgcgt caatgtcatg ttctgcgacg cccatacgga tacgatctcg     1560
gacctgttcg atgttctttg tctcaatcgg tactatgggt ggtatgttca gagcggggat     1620
cttgagacgg cggagaaggt tcttgagaag gaactcctgg cgtggcaaga gaagctccat     1680
cagccgatca ttatcacgga gtacggggtt gacacacttg cgggccttca cagtatgtac     1740
acagatatgt ggtcggagga ataccagtgt gcatggttgg atatgtacca tcgtgtcttc     1800
gaccgggttt cagcggttgt cggcgaacaa gtctggaact tcgcagactt cgccacgagc     1860
caagggatac tgcgggtagg agggaacaag aagggaatct tcacacggga tcggaagccc     1920
aagtcagcag ccttcctgtt gcagaagcga tggacaggaa tgaacttcgg agaaaagcca     1980
cagcaaggcg gaaagcagtg a                                                2001
```

US 11,932,863 B2

PLANT REGULATORY ELEMENTS AND USES THEREOF

REFERENCE TO RELATED APPLICATION

This application claims the benefit of U.S. Provisional Application Ser. No. 62/969,993, filed Feb. 4, 2020, which is herein incorporated by reference in its entirety.

INCORPORATION OF SEQUENCE LISTING

The sequence listing that is contained in the file named "MONS479US_ST25.txt", is 42,265 bytes (as measured in Microsoft Windows®), was created on Jan. 5, 2021, and is filed herewith by electronic submission and incorporated by reference herein.

FIELD OF THE INVENTION

The invention relates to the field of plant molecular biology and plant genetic engineering. More specifically, the invention relates to DNA molecules useful for modulating gene expression in plants.

BACKGROUND

Regulatory elements are genetic elements that regulate gene activity by modulating the transcription of an operably linked transcribable DNA molecule. Such elements may include promoters, leaders, introns, and 3' untranslated regions and are useful in the field of plant molecular biology and plant genetic engineering.

SUMMARY OF THE INVENTION

The invention provides gene regulatory elements for use in plants. The invention also provides recombinant DNA molecules comprising the regulatory elements. The present invention also provides transgenic plant cells, plants, and seeds comprising the regulatory elements. In one embodiment, the regulatory elements are operably linked to a transcribable DNA molecule. In certain embodiments, the transcribable DNA molecule may be heterologous with respect to the regulatory sequence. Thus, a regulatory element sequence provided by the invention may, in particular embodiments, be defined as operably linked to a heterologous transcribable DNA molecule. The present invention also provides methods of using the regulatory elements and making and using the recombinant DNA molecules comprising the regulatory elements, and the transgenic plant cells, plants, and seeds comprising the regulatory elements operably linked to a transcribable DNA molecule.

Thus, in one aspect, the invention provides a recombinant DNA molecule comprising a DNA sequence selected from the group consisting of: (a) a sequence with at least about 85 percent sequence identity to any of SEQ ID NOs:1-20; (b) a sequence comprising any of SEQ ID NOs:1-20; and (c) a fragment of any of SEQ ID NOs:1-20, wherein the fragment has gene-regulatory activity; wherein the sequence is operably linked to a heterologous transcribable DNA molecule. By "heterologous transcribable DNA molecule," it is meant that the transcribable DNA molecule is heterologous with respect to the polynucleotide sequence to which it is operably linked. In specific embodiments, the recombinant DNA molecule comprises a DNA sequence having at least about 85 percent, at least about 86 percent, at least about 87 percent, at least about 88 percent, at least about 89 percent, at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs:1-20.

In another aspect, provided herein are transgenic plant cells comprising a recombinant DNA molecule comprising a DNA sequence selected from the group consisting of: (a) a sequence with at least about 85 percent sequence identity to any of SEQ ID NOs:1-20; (b) a sequence comprising any of SEQ ID NOs:1-20; and (c) a fragment of any of SEQ ID NOs:1-20, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: a) a sequence with at least 85 percent sequence identity to any of SEQ ID NOs:1-20; b) a sequence comprising any of SEQ ID NOs:1-20; and c) a fragment of any of SEQ ID NOs:1-20, wherein the fragment has gene-regulatory activity; wherein the sequence is operably linked to a heterologous transcribable DNA molecule. In specific embodiments, the transgenic plant is a progeny plant of any generation that comprises the recombinant DNA molecule. A transgenic seed comprising the recombinant DNA molecule that produces such a transgenic plant when grown is also provided.

In another aspect, the invention provides a method of producing a commodity product comprising obtaining a transgenic plant or part thereof containing a recombinant DNA molecule of the invention and producing the commodity product therefrom. In one embodiment, the commodity product is seeds, processed seeds, protein concentrate, protein isolate, starch, grains, plant parts, seed oil, biomass, flour and meal.

In still yet another aspect, the invention provides a method of producing a transgenic plant comprising a recombinant DNA molecule of the invention comprising transforming a plant cell with the recombinant DNA molecule of the invention to produce a transformed plant cell and regenerating a transgenic plant from the transformed plant cell.

BRIEF DESCRIPTION OF THE SEQUENCES

SEQ ID NO:1 is a DNA sequence of a promoter operably linked to a leader, P-Zm.GRMZM2G487322:2, derived from *Zea mays*.

SEQ ID NO:2 is a DNA sequence of a 3' UTR, T-Zm.GRMZM2G487322:2, derived from *Zea mays*.

SEQ ID NO:3 is a DNA sequence of a promoter operably linked to a leader, P-Zm.GRMZM2G339781:1, derived from *Zea mays*.

SEQ ID NO:4 is a DNA sequence of a 3' UTR, T-Zm.GRMZM2G339781:1, derived from *Zea mays*.

SEQ ID NO:5 is a DNA sequence of a regulatory expression element group or EXP, EXP-Zm.Xet:1, comprised of a promoter operably linked to leader (P-Zm.Xet:1), operably linked to an intron (I-Zm.Xet:1), derived from *Zea mays*.

SEQ ID NO:6 is a DNA sequence of a promoter operably linked to a leader, P-Zm.Xet:1, derived from *Zea mays*.

SEQ ID NO:7 is a DNA sequence of an intron, I-Zm.Xet:1, derived from *Zea mays*.

SEQ ID NO:8 is a DNA sequence of a 3' UTR, T-Zm.Xet:1, derived from *Zea mays*.

SEQ ID NO:9 is a DNA sequence of an EXP, EXP-Zm.Sat6:1, comprised of a promoter operably linked to leader (P-Zm.Sat6:1), operably linked to an intron (I-Zm.Sat6:1), derived from *Zea mays*.

SEQ ID NO:10 is a DNA sequence of a promoter operably linked to a leader, P-Zm.Sat6:1, derived from *Zea mays*.

SEQ ID NO:11 is a DNA sequence of an intron, I-Zm.Sat6:1, derived from *Zea mays*.

SEQ ID NO:12 is a DNA sequence of a 3' UTR, T-Zm.Sat6:1, derived from *Zea mays*.

SEQ ID NO:13 is a DNA sequence of an EXP, EXP-Zm.GRMZM2G049726:1, comprised of a promoter operably linked to leader (P-Zm.GRMZM2G049726:1), operably linked to an intron (I-Zm.GRMZM2G049726:1), derived from *Zea mays*.

SEQ ID NO:14 is a DNA sequence of a promoter operably linked to a leader, P-Zm.GRMZM2G049726:1, derived from *Zea mays*.

SEQ ID NO:15 is a DNA sequence of an intron, I-Zm.GRMZM2G049726:1, derived from *Zea mays*.

SEQ ID NO:16 is a DNA sequence of a 3' UTR, T-Zm.GRMZM2G049726:1, derived from *Zea mays*.

SEQ ID NO:17 is a DNA sequence of a promoter operably linked to a leader, P-Zm.GRMZM2G141762:1, derived from *Zea mays*.

SEQ ID NO:18 is a DNA sequence of a promoter operably linked to a leader, P-Zm.DSUL:1, derived from *Zea mays*.

SEQ ID NO:19 is a DNA sequence of a promoter operably linked to a leader, P-Zm.GRMZM2G512113:1, derived from *Zea mays*.

SEQ ID NO:20 is a DNA sequence of a 3' UTR, T-Zm.GRMZM2G512113:1, derived from *Zea mays*.

SEQ ID NO:21 is a synthetic coding sequence optimized for plant expression for β-glucuronidase (GUS, GOI-Ec.uidA+St.LS1.nno:1) with a processable intron derived from the potato light-inducible, tissue-specific St-LS1 gene (Genbank Accession: X04753).

DETAILED DESCRIPTION OF THE INVENTION

The invention provides regulatory elements having gene-regulatory activity in plants. The nucleotide sequences of these regulatory elements are provided as SEQ ID NOs:1-20. These regulatory elements are capable of affecting the expression of an operably linked transcribable DNA molecule in plant tissues, and therefore regulating gene expression of an operably linked transgene in transgenic plants. The invention also provides methods of modifying, producing, and using recombinant DNA molecules which contain the provided regulatory elements. The invention also provides compositions that include transgenic plant cells, plants, plant parts, and seeds containing the recombinant DNA molecules of the invention, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a DNA molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, a DNA molecule that comprises a synthetic DNA sequence or a DNA molecule that has been incorporated into a host cell's DNA by genetic transformation or gene editing.

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another sequence, to maximize the number of nucleotide matches in the sequence alignment with appropriate internal nucleotide insertions, deletions, or gaps. As used herein, the term "reference sequence" refers to a DNA sequence provided as SEQ ID NOs:1-20.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that, when optimally aligned to a reference sequence, provided herein as SEQ ID NOs:1-20, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering.

As used herein, a "regulatory expression element group" or "EXP" sequence may refer to a group of operably linked regulatory elements, such as enhancers, promoters, leaders, and introns. For example, a regulatory expression element group may be comprised, for instance, of a promoter operably linked 5' to a leader sequence, operably linked 5' to an intron sequence. EXP's useful in practicing the present invention include SEQ ID NOs:5, 9, and 13.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), a small interfering RNA (siRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially isolated from the 5' untranslated region (5' UTR) of a genomic copy of a gene, or for the purposes of this disclosure, promoters provided herein are comprised of a promoter operably linked 5' to the leader. Alternately, promoters may be synthetically produced or manipulated DNA molecules. Promoters may also be chimeric. Chimeric promoters are produced through the fusion of two or more heterologous DNA molecules. Promoters useful in practicing the present invention include promoter elements comprised within any of SEQ ID NOs:1, 3, 5, 6, 9, 10, 13, 14, 17, 18, and 19, or fragments or variants thereof. In specific embodiments of the invention, the claimed DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments of a promoter sequence disclosed herein are provided. Promoter fragments may comprise promoter activity, as described above, and may be useful alone or in combination with other promoters and promoter fragments, such as in constructing chimeric promoters, or in combination with other expression elements and expression element fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. Methods for producing such fragments from a starting promoter molecule are well known in the art.

Compositions derived from any of the promoter elements comprised within any of SEQ ID NOs:1, 3, 5, 6, 9, 10, 13, 14, 17, 18, and 19 such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Compositions derived from any of the promoter elements comprised within any of SEQ ID NOs:1, 3, 5, 6, 9, 10, 13, 14, 17, 18, and 19, comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm) effects on expression. Any of the promoter elements provided as comprised within any of SEQ ID NOs:1, 3, 5, 6, 9, 10, 13, 14, 17, 18, and 19 and fragments or enhancers derived therefrom can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Leaders useful in practicing the present invention include leader elements comprised within any of SEQ ID NOs:1, 3, 5, 6, 9, 10, 13, 14, 17, 18, and 19 or fragments or variants thereof. In specific embodiments, such DNA sequences may be defined as being capable of acting as a leader in a host cell, including, for example, a transgenic plant cell. In one embodiment, such sequences are decoded as comprising leader activity.

The leader sequences (also referred to as 5' UTRs) comprised within any of SEQ ID NOs:1, 3, 5, 6, 9, 10, 13, 14, 17, 18, and 19 may be comprised of regulatory elements, or may adopt secondary structures that can have an effect on transcription or translation of an operably linked transcribable DNA molecule. The leader sequences comprised within any of SEQ ID NOs:1, 3, 5, 6, 9, 10, 13, 14, 17, 18, and 19 can be used in accordance with the invention to make chimeric regulatory elements that affect transcription or translation of a an operably linked transcribable DNA molecule.

As used herein, the term "intron" refers to a DNA molecule that may be isolated or identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements. Exemplary introns useful in practicing the present invention are presented as SEQ ID NOs:7, 11, and 15.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region, wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. First, the 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. Second, the 3' UTR should not cause a reduction in the transcriptional activity imparted by the promoter, leader, enhancers, and introns that are used to drive expression of the DNA molecule. Finally, in plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette. 3' UTRs useful in practicing the present invention are presented as SEQ ID NO:2, 4, 8, 12, 16, and 20.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention. Enhancers can be derived from any of the promoters comprised within SEQ ID NOs:1, 3, 5, 6, 9, 10, 13, 14, 17, 18, and 19.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments for example, the fusion of a promoter to an enhancer element. Thus, the design, construction, and use of chimeric promoters according to the methods disclosed herein for modulating the expression of operably linked transcribable DNA molecules are encompassed by the present invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, the DNA sequences provided as SEQ ID NOs:1-20 may provide regulatory element reference sequences, wherein the constituent elements that comprise the reference sequence may be joined by methods known in the art and may comprise substitutions, deletions, and/or insertions of one or more nucleotides or mutations that naturally occur in bacterial and plant cell transformation.

As used herein, the term "variant" refers to a second DNA molecule, such as a regulatory element, that is in composition similar, but not identical to, a first DNA molecule, and wherein the second DNA molecule still maintains the general functionality, i.e. the same or similar expression pattern, for instance through more or less equivalent transcriptional activity, of the first DNA molecule. A variant may be a shorter or truncated version of the first DNA molecule or an altered version of the sequence of the first DNA molecule, such as one with different restriction enzyme sites and/or internal deletions, substitutions, or insertions. A "variant" can also encompass a regulatory element having a nucleotide sequence comprising a substitution, deletion, or insertion of one or more nucleotides of a reference sequence, wherein the derivative regulatory element has more or less or equivalent transcriptional or translational activity than the corresponding parent regulatory molecule. Regulatory element "variants" will also encompass variants arising from mutations that naturally occur in bacterial and plant cell transformation. In the present invention, a polynucleotide sequence provided as SEQ ID NOs:1-20 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404, however other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA Molecules

As used herein, the term "transcribable DNA molecule" refers to any DNA molecule capable of being transcribed into a RNA molecule, including, but not limited to, those having protein coding sequences, those encoding guide RNAs, and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs:1-20, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (U.S. Pat. Nos. 6,803, 501; 6,448,476; 6,248,876; 6,225,114; 6,107,549; 5,866, 775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653, 280; 6,573,361; 6,506,962; 6,316,407; 6,215,048; 5,516, 671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444, 876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822, 141; 6,770,465; 6,706,950; 6,660,849; 6,596,538; 6,589, 767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; and U.S. Pat. Nos. 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229, 114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998, 700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance. An example of a selectable marker transgene is provided as SEQ ID NO:21.

Genome Editing

Several embodiments relate to a recombinant DNA construct comprising an expression cassette(s) comprising a sequence with at least about 85 percent sequence identity to any of SEQ ID NOs:1-20 or a fragment thereof operably linked to a heterologous DNA sequence encoding a site-specific genome modification enzyme and/or any associated protein(s) to carry out genome modification. These nuclease-expressing cassette(s) may be present in the same molecule or vector as a donor template for templated editing (in cis) or on a separate molecule or vector (in trans). Several methods for editing are known in the art involving different sequence-specific genome modification enzymes (or complexes of proteins and/or guide RNA) that modify the genomic DNA. In some embodiments, a site-specific genome modification enzyme modifies the genome by inducing a double-strand break (DSB) or nick at a desired genomic site or locus. In some embodiments, during the process of repairing the DSB or nick introduced by the genome modification enzyme, a donor template DNA may become integrated into the genome at the site of the DSB or nick. In some embodiments, during the process of repairing the DSB or nick introduced by the genome modification enzyme, an insertion or deletion mutation (indel) may be introduced into the genome. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases, reverse transcriptases and any combination thereof.

Several embodiments relate to a gene regulatory element as described herein operably linked to a heterologous transcribable DNA molecule encoding one or more components of a genome editing system. Genome editing systems may be used to introduce one or more insertions, deletions, substitutions, base modifications, translocations, or inversions to a genome of a host cell. In some embodiments, a gene regulatory element as described herein is operably linked to a heterologous transcribable DNA molecule encoding a sequence-specific DNA binding domain, such as a CRISPR-Cas effector protein, a zinc finger protein, or a transcription activator (TAL) protein. In some embodiments, the sequence-specific DNA binding domain maybe a fusion protein. In some embodiments, a gene regulatory element as described herein is operably linked to a heterologous transcribable DNA molecule encoding a CRISPR-Cas effector protein. In some embodiments, the CRISPR-Cas effector protein is selected from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a gene regulatory element as described herein is operably linked to a heterologous transcribable DNA molecule encoding a guide RNA. As used herein, a "guide RNA" or "gRNA" refers to an RNA that recognizes a target DNA sequence and directs, or "guides", a CRISPR effector protein to the target DNA sequence. A guide RNA is comprised of a region that is complementary to the target DNA (referred to as the crRNA) and a region that binds the CRISPR effector protein (referred to as the tracrRNA). A guide RNA may be a single RNA molecule (sgRNA) or two separate RNAs molecules (a 2-piece gRNA). In some embodiments a gRNA may further comprise an RNA template (pegRNA) for a reverse transcriptase.

Several embodiments relate to a gene regulatory element as described herein operably linked to a heterologous transcribable DNA molecule encoding one or more components of a CRISPR-Cas genome editing system comprising a CRISPR-Cas effector protein and a guide RNA. Examples of CRISPR-Cas effector proteins include, but are not limited to, Cas9, C2c1, C2c3, C2c4, C2c5, C2c8, C2c9, C2c10, Cas12a (also referred to as Cpf1), Cas12b, Cas12c, Cas12d, Cas12e, Cas12h, Cas12i, Cas12g, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), Csf5, Cas14a, Cas14b, and Cas14c effector protein. In some embodiments, a gene regulatory element as described herein is operably linked to a CRISPR-Cas effector protein comprising a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation. In some embodiments, a gene regulatory element as described herein is operably linked to a CRISPR-Cas effector protein having a mutation in its nuclease active site to generate a nickase activity operably linked to a reverse transcriptase enzyme.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), gene editing (e.g., CRISPR-Cas systems), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, CA, 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique*, (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs:1-20. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown is to be interpreted as illustrative and not in a limiting sense.

EXAMPLES

Example 1

Identification and Cloning of the Regulatory Elements

This Example describes the identification, synthesis, and cloning of regulatory expression elements derived from *Zea mays*.

Genes with a preference for expression in the pollen were identified using public and proprietary transcriptome data. Each gene locus was examined bioinformatically and the corresponding gene promoters, leaders, introns, and 3' UTR's were identified. The identified EXPs, promoters/leaders, introns, and 3' UTRs are presented in Table 1 below.

TABLE 1

Regulatory expression element groups, promoters, leaders, introns, and 3' UTRs.

| Annotation | SEQ ID NO: | Size (bp) | Description and/or regulatory elements of EXP linked in 5' → 3' direction (SEQ ID NOs): |
|---|---|---|---|
| P-Zm.GRMZM2G487322:2 | 1 | 1973 | Promoter + Leader |
| T-Zm.GRMZM2G487322:2 | 2 | 501 | 3' UTR |
| P-Zm.GRMZM2G339781:1 | 3 | 1998 | Promoter + Leader |
| T-Zm.GRMZM2G339781:1 | 4 | 501 | 3' UTR |
| EXP-Zm.Xet:1 | 5 | 2196 | EXP: P-Zm.Xet:1 (SEQ ID NO: 6, I-Zm.Xet:1 (SEQ ID NO: 7) |
| P-Zm.Xet:1 | 6 | 1998 | Promoter |
| I-Zm.Xet:1 | 7 | 191 | Intron |
| T-Zm.Xet: 1 | 8 | 498 | 3' UTR |
| EXP-Zm.Sat6:1 | 9 | 2183 | EXP: P-Zm.Sat6:1 (SEQ ID NO: 10, I-Zm.Sat6:1 (SEQ ID NO: 11) |
| P-Zm.Sat6:1 | 10 | 1998 | Promoter |
| I-Zm.Sat6:1 | 11 | 178 | Intron |
| T-Zm.Sat6:1 | 12 | 498 | 3' UTR |
| EXP-Zm.GRMZM2G049726:1 | 13 | 2145 | EXP: P-Zm.GRMZM2G049726:1 (SEQ ID NO: 14), I-Zm.GRMZM2G049726:1 (SEQ ID NO: 15) |

TABLE 1-continued

Regulatory expression element groups, promoters, leaders, introns, and 3' UTRs.

| Annotation | SEQ ID NO: | Size (bp) | Description and/or regulatory elements of EXP linked in 5' → 3' direction (SEQ ID NOs): |
|---|---|---|---|
| P-Zm.GRMZM2G049726:1 | 14 | 1998 | Promoter |
| I-Zm.GRMZM2G049726:1 | 15 | 140 | Intron |
| T-Zm.GRMZM2G049726:1 | 16 | 501 | 3' UTR |
| P-Zm.GRMZM2G141762:1 | 17 | 1998 | Promoter + Leader |
| P-Zm.DSUL:1 | 18 | 1568 | Promoter + Leader |
| P-Zm.GRMZM2G512113:1 | 19 | 2000 | Promoter + Leader |
| T-Zm.GRMZM2G512113:1 | 20 | 704 | 3' UTR |

The identified EXPs, promoters/leaders, and 3' UTRs were synthesized and cloned using methods known in the art into binary plants transformation vector constructs, in an expression cassette used to drive β-glucuronidase (GUS) expression to assess their activity in stably transformed corn plants, as described in Example 2 below.

Example 2

Analysis of Regulatory Elements Driving GUS Expression in Stably Transformed Corn Plants Corn plants were transformed with a vector, specifically a plant expression vector containing test regulatory elements driving expression of the β-glucuronidase (GUS) transgene. The resulting plants were analyzed for GUS protein expression, to assess the effect of the selected regulatory element on expression.

Corn plants were transformed with plant GUS expression constructs. The regulatory elements were cloned into a base plant expression vector using standard methods known in the art. The resulting plant expression vectors contained a left border region from *Agrobacterium tumefaciens* (B-AGRtu.left border), a first transgene selection cassette used for selection of transformed plant cells that confers resistance to the herbicide glyphosate, a second transgene cassette to assess the activity of the regulatory elements comprised of a promoter and leader, optionally operably linked 5' to an intron in certain vector designs, operably linked to a coding sequence for GUS comprised of a processable intron (SEQ ID NO:21), operably linked to a 3' UTR, and a right border region from *Agrobacterium tumefaciens* (B-AGRtu.right border).

The expression element configurations for the GUS expression cassettes for each construct are presented in Table 2. Construct-1 through Construct-5 comprise GUS expression cassettes comprised of the native promoter and leader operably linked (indicated as "P–") or the native promoter, leader, and intron operably linked (indicated as "EXP–"). The GUS expression cassettes of Construct-1 and Construct-2 do not comprise an intron. Construct-1 through Construct-5 and Construct-8 comprise the native 3' UTR of the same gene locus promoter/leader or promoter/leader/intron. In Construct-6 and Construct-7, the native promoter and leader (indicated as "P–"), were operably linked to a plant expressable intron and 3' UTR that were not part of the native gene. Construct-8 also comprises a plant expressable intron that was not part of the native gene.

TABLE 2

GUS expression cassette configuration for Construct-1 through Construct-7.

| Construct | EXP or Promoter/Leader | EXP or Promoter/Leader SEQ ID NO: | 3' UTR | 3' UTR SEQ ID NO: |
|---|---|---|---|---|
| Construct-1 | P-Zm.GRMZM2G487322:2 (No intron) | 1 | T-Zm.GRMZM2G487322:2 | 2 |
| Construct-2 | P-Zm.GRMZM2G339781:1 (No Intron) | 3 | T-Zm.GRMZM2G339781:1 | 4 |
| Construct-3 | EXP-Zm.Xet:1 | 5 | T-Zm.Xet:1 | 8 |
| Construct-4 | EXP-Zm.Sat6:1 | 9 | T-Zm.Sat6:1 | 12 |
| Construct-5 | EXP-Zm.GRMZM2G049726:1 | 13 | T-Zm.GRMZM2G049726:1 | 16 |
| Construct-6 | P-Zm.GRMZM2G141762:1 + Plant Intron | 17 | Plant 3' UTR | |
| Construct-7 | P-Zm.DSUL:1 + Plant Intron | 18 | Plant 3' UTR | |
| Construct-8 | P-Zm.GRMZM2G512113:1 + Plant Intron | 19 | T-Zm.GRMZM2G512113:1 | 20 |

Corn plant cells were transformed using the binary transformation vector constructs described above by *Agrobacterium*-mediated transformation, as is well known in the art. The resulting transformed plant cells were induced to form whole corn plants.

Qualitative and quantitative GUS analysis was used to evaluate expression element activity in selected plant organs and tissues in transformed plants. For qualitative analysis of GUS expression by histochemical staining, whole-mount or sectioned tissues were incubated with GUS staining solution containing 1 mg/mL of X-Gluc (5-bromo-4-chloro-3-indolyl-b-glucuronide) for 5 h at 37° C. and de-stained with 35% EtOH and 50% acetic acid. Expression of GUS was qualitatively determined by visual inspection of selected plant organs or tissues for blue coloration under a dissecting or compound microscope.

For quantitative analysis of GUS expression by enzymatic assays, total protein was extracted from selected tissues of transformed corn plants. One to two micrograms of total protein was incubated with the fluorogenic substrate, 4-methyleumbelliferyl-β-D-glucuronide (MUG) at 1 mM concentration in a total reaction volume of 50 microliters. After 1 h incubation at 37° C., the reaction was stopped by adding 350 microliters of 200 mM sodium bicarbonate solution. The reaction product, 4-methylumbelliferone (4-MU), is maximally fluorescent at high pH, where the hydroxyl group is ionized. Addition of the basic sodium carbonate solution simultaneously stops the assay and adjusts the pH for quantifying the fluorescent product 4-MU. The amount of 4-MU formed was estimated by measuring its fluorescence using a FLUOstar Omega Microplate Reader (BMG LABTECH) (excitation at 355 nm, emission at 460 nm). GUS activity values are provided in nmoles of 4-MU/hour/mg total protein.

The following tissues were sampled for GUS expression in the $R_0$ generation: V4 stage Leaf and Root; V7 stage Leaf and Root; VT stage Leaf, Flower/Anther, and Pollen; R1 stage Cob/Silk; and R3 stage Seed Embryo and Seed Endosperm 21 days after pollination (DAP).

Tables 3 and 4 show the mean quantitative GUS expression for the sampled tissues, wherein "bdl" indicates below detection level and "NA" indicates not assayed. The ranges of GUS expression for VT stage Flower/Anther and Pollen, and R1 stage Cob/Silk are also presented in Table 4.

TABLE 3

Mean GUS expression of stably transformed corn plants for V4 stage Leaf and Root; V7 stage Leaf and Root; VT stage Leaf; and 21 DAP Embryo and Endosperm.

| Construct | V4 Root | V4 Leaf | V7 Root | V7 Leaf | VT Leaf | 21 DAP embryo | 21 DAP endosperm |
|---|---|---|---|---|---|---|---|
| Construct-1 | 23 | 25 | 30 | 24 | 24 | 40 | 22 |
| Construct-2 | 39 | 37 | 39 | 40 | 22 | 49 | 37 |
| Construct-3 | 22 | 27 | 75 | 59 | bdl | NA | NA |
| Construct-4 | 36 | 40 | 37 | 36 | 22 | 48 | 41 |
| Construct-5 | 22 | 30 | 27 | 28 | 25 | 28 | 23 |
| Construct-6 | 103 | 62 | 39 | 53 | 42 | 329 | 332 |
| Construct-7 | 70 | 49 | 48 | 35 | 42 | 41 | 50 |
| Construct-8 | 46 | bdl | 25 | bdl | bdl | 20 | 71 |

TABLE 4

Mean GUS and range of expression of stably transformed corn plants for VT Fowers/Anthers and Pollen, and R1 Cob/Silk.

| Construct | VT Flower, anthers | VT Flower, pollen | R1 Cob, silk | VT Flower, anthers range | VT Flower, pollen Range | R1 Cob, silk range |
|---|---|---|---|---|---|---|
| Construct-1 | 433 | 1202 | 23 | 27-2731 | 189-3998 | 23-24 |
| Construct-2 | 434 | 1040 | bdl | 21-1228 | 47-1965 | bdl |
| Construct-3 | 60 | 274 | 29 | 27-114 | 53-606 | 21-39 |
| Construct-4 | 27 | 110 | bdl | 21-39 | 77-139 | bdl |
| Construct-5 | 25 | 91 | 23 | 21-28 | 44-241 | 44-241 |
| Construct-6 | 1182 | NA | NA | 634-1897 | NA | NA |
| Construct-7 | 987 | NA | 1265 | 509-1279 | NA | 568-2151 |
| Construct-8 | 63 | NA | bdl | 31-114 | NA | bdl |

As can be seen in Tables 3 and 4 many of the GUS expression cassettes in each of the constructs demonstrated higher expression in the VT Flowers/Anther and/or Pollen with the exception of Construct-6 and Construct-7. With respect to Construct-6, high expression was quantitatively measured in the VT Anther, and 21 DAP Embryo and Endosperm. For Construct-7, high expression of GUS was quantitatively measured in the VT Anther and R1 Cob/Silk. For Construct-8, VT Anther expression was lower relative to Construct-6 and Construct-7. VT Pollen GUS expression was not determined quantitatively for Construct-6, Construct-7, and Construct-8. Construct-1 and Construct-2 demonstrated high GUS expression in VT Pollen with a higher GUS expression in the VT Flower/Anther than other tissues.

Selected tissues from the transformed events were also viewed microscopically to determine aspect of the qualitative expression observed in GUS staining of the tissues. Table 5 below summarizes the observations made of these tissues.

TABLE 5

Qualitative GUS expression of stably transformed corn plants.

| Construct | Qualitative GUS Expression |
|---|---|
| Construct-1 | Staining in anther is associated with the pollen. |
| Construct-2 | Staining in anther is associated with the pollen. |
| Construct-3 | Staining in anther is associated with the pollen. |
| Construct-4 | Staining in anther is associated with the pollen. |
| Construct-5 | Staining in anther is associated with the pollen. |
| Construct-6 | Visible staining in VT pollen, glume/palea, and pedicel; V7 Leaf mesophyll, bundle sheath, vascular bundle, and guard cells; V7 root cortex, endodermis, epidermis, and pericycle. |
| Construct-7 | Visible staining in VT pollen, glume/palea, and pedicel; R1 silk; V7 Leaf mesophyll, bundle sheath, vascular bundle, and guard cells; V7 root cortex, endodermis, epidermis, and pericycle. |
| Construct-8 | Visible staining in VT pollen; V4 root tip; R3 basal endosperm transfer cell layer, aleurone, embryo, endosperm, pedicel, pericarp, and scutellum. |

As can be seen in Table 5, GUS expression for Construct-1 through Construct-5 was primarily observed in the VT Pollen and thus provided higher expression in the VT Flower/Anther when measured quantitatively. The expression elements in the GUS expression cassettes of Construct-1 through Construct-5 are therefore "pollen-preferred" expression elements. With respect to GUS expression from Construct-6 and Construct-7, GUS expression was observed not only in the VT Pollen, but other tissues as well such as cells in the V7 Leaf and Root. Interestingly, GUS expression from Construct-7 was also seen in the R1 silk. For Construct-8 VT pollen staining was clearly visible, as well as, staining in the V4 root tip and R3 21DAP embryo and endosperm tissues.

Thus, the expression elements comprised within the GUS expression cassettes of Construct-1 through Construct-5 demonstrate a pollen-preferred expression pattern. The expression elements comprised within the GUS expression cassettes of Construct-6, Construct-7 and Construct-8, while demonstrating expression in the pollen, also express in other tissues of the stably transformed corn plants.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:
   a) a sequence with at least 99 percent sequence identity to SEQ ID NO: 1, wherein the sequence has promoter activity;
   b) a sequence comprising SEQ ID NO: 1; and
   c) a fragment comprising at least 150 contiguous nucleotides of SEQ ID NO: 1, wherein the fragment has promoter activity;
   wherein said sequence is operably linked to a heterologous transcribable DNA molecule.

2. The recombinant DNA molecule of claim 1, wherein said sequence comprises SEQ ID NO: 1.

3. The recombinant DNA molecule of claim 1, wherein the heterologous transcribable DNA molecule comprises a gene of agronomic interest.

4. The recombinant DNA molecule of claim 3, wherein the gene of agronomic interest confers herbicide tolerance in plants.

5. The recombinant DNA molecule of claim 3, wherein the gene of agronomic interest confers pest resistance in plants.

6. The recombinant DNA molecule of claim 1, wherein the heterologous transcribable DNA molecule encodes an dsRNA, an miRNA, or a siRNA.

7. A transgenic plant cell comprising a recombinant DNA molecule comprising a sequence selected from the group consisting of:
   a) a sequence with at least 99 percent sequence identity to SEQ ID NO: 1, wherein the sequence has promoter activity;
   b) a sequence comprising SEQ ID NO: 1; and
   c) a fragment comprising at least 150 contiguous nucleotides of SEQ ID NO: 1, wherein the fragment has promoter activity;
   wherein said sequence is operably linked to a heterologous transcribable DNA molecule.

8. The transgenic plant cell of claim 7, wherein said transgenic plant cell is a monocotyledonous plant cell.

9. The transgenic plant cell of claim 7, wherein said transgenic plant cell is a dicotyledonous plant cell.

10. A transgenic plant, or part thereof, comprising the recombinant DNA molecule of claim 1.

11. A progeny plant of the transgenic plant of claim 10, or a part thereof, wherein the progeny plant or part thereof comprises said recombinant DNA molecule.

12. A transgenic seed, wherein the seed comprises the recombinant DNA molecule of claim 1.

13. A method of producing a commodity product comprising obtaining a transgenic plant or part thereof according to claim 10 and producing the commodity product therefrom.

14. The method of claim 13, wherein the commodity product is seeds, processed seeds, protein concentrate, protein isolate, starch, grains, plant parts, seed oil, biomass, flour and meal.

15. A method of expressing a transcribable DNA molecule comprising obtaining a transgenic plant according to claim 10 and cultivating plant, wherein the transcribable DNA is expressed.

* * * * *